United States Patent
Friedman et al.

(10) Patent No.: US 12,263,118 B2
(45) Date of Patent: Apr. 1, 2025

(54) SYSTEMS AND METHODS FOR IMPLANTABLE DEVICES

(71) Applicant: Mayo Foundation for Medical Education and Research, Rochester, MN (US)

(72) Inventors: Paul A. Friedman, Rochester, MN (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1117 days.

(21) Appl. No.: 16/249,159

(22) Filed: Jan. 16, 2019

(65) Prior Publication Data

US 2019/0216641 A1    Jul. 18, 2019

Related U.S. Application Data

(60) Provisional application No. 62/618,432, filed on Jan. 17, 2018.

(51) Int. Cl.
| | |
|---|---|
| *A61F 7/12* | (2006.01) |
| *A61B 5/00* | (2006.01) |
| *A61B 5/287* | (2021.01) |
| *A61B 5/361* | (2021.01) |
| *A61F 5/00* | (2006.01) |
| *A61F 7/00* | (2006.01) |

(52) U.S. Cl.
CPC ............... *A61F 7/12* (2013.01); *A61B 5/287* (2021.01); *A61B 5/361* (2021.01); *A61B 5/4836* (2013.01); *A61B 5/686* (2013.01); *A61F 5/0013* (2013.01); *A61F 2005/002* (2013.01); *A61F 2007/0093* (2013.01); *A61F 2007/126* (2013.01)

(58) Field of Classification Search
CPC .... A61F 7/12; A61F 5/0013; A61F 2005/002; A61F 2007/0093; A61F 2007/126; A61B 5/287; A61B 5/361; A61B 5/4836; A61B 5/686

See application file for complete search history.

(56) References Cited

U.S. PATENT DOCUMENTS

| | | | |
|---|---|---|---|
| 6,090,145 A | 7/2000 | Hassler et al. | |
| 2002/0198526 A1 | 12/2002 | Shaolian et al. | |
| 2008/0195161 A1* | 8/2008 | Sakuma | ............... A61N 1/0587 607/113 |
| 2009/0299216 A1 | 12/2009 | Chen et al. | |
| 2011/0218476 A1* | 9/2011 | Kraemer | ........... A61M 25/0068 604/8 |

(Continued)

FOREIGN PATENT DOCUMENTS

WO    WO 2017/096133    6/2017

OTHER PUBLICATIONS

U.S. Appl. No. 16/238,374, filed Jan. 2, 2019, Paul A. Friedman.

*Primary Examiner* — Eun Hwa Kim
*Assistant Examiner* — Catherine C Premraj
(74) *Attorney, Agent, or Firm* — Fish & Richardson P.C.

(57) ABSTRACT

This document describes methods and materials for the treatment of pathological conditions, including arrhythmias and trauma, using temperature modulation via implantable devices. For example, this document relates to methods and devices for treating atrial and/or ventricular fibrillation by cooling the epicardium.

20 Claims, 2 Drawing Sheets

(56) References Cited

U.S. PATENT DOCUMENTS

| | | | |
|---|---|---|---|
| 2012/0053660 A1* | 3/2012 | Dobak, III | A61N 1/36167 607/72 |
| 2012/0277742 A1* | 11/2012 | Laufer | A61B 17/30 606/45 |
| 2012/0290023 A1* | 11/2012 | Boyden | A61F 7/007 607/3 |
| 2015/0342675 A1* | 12/2015 | Highsmith | A61B 18/1492 606/41 |
| 2016/0051322 A1* | 2/2016 | Asirvatham | A61N 1/0551 606/41 |
| 2017/0156616 A1* | 6/2017 | Talkachova | A61B 5/316 |
| 2017/0224986 A1* | 8/2017 | Imran | A61N 1/36007 |
| 2019/0217110 A1 | 7/2019 | Friedman et al. | |

* cited by examiner

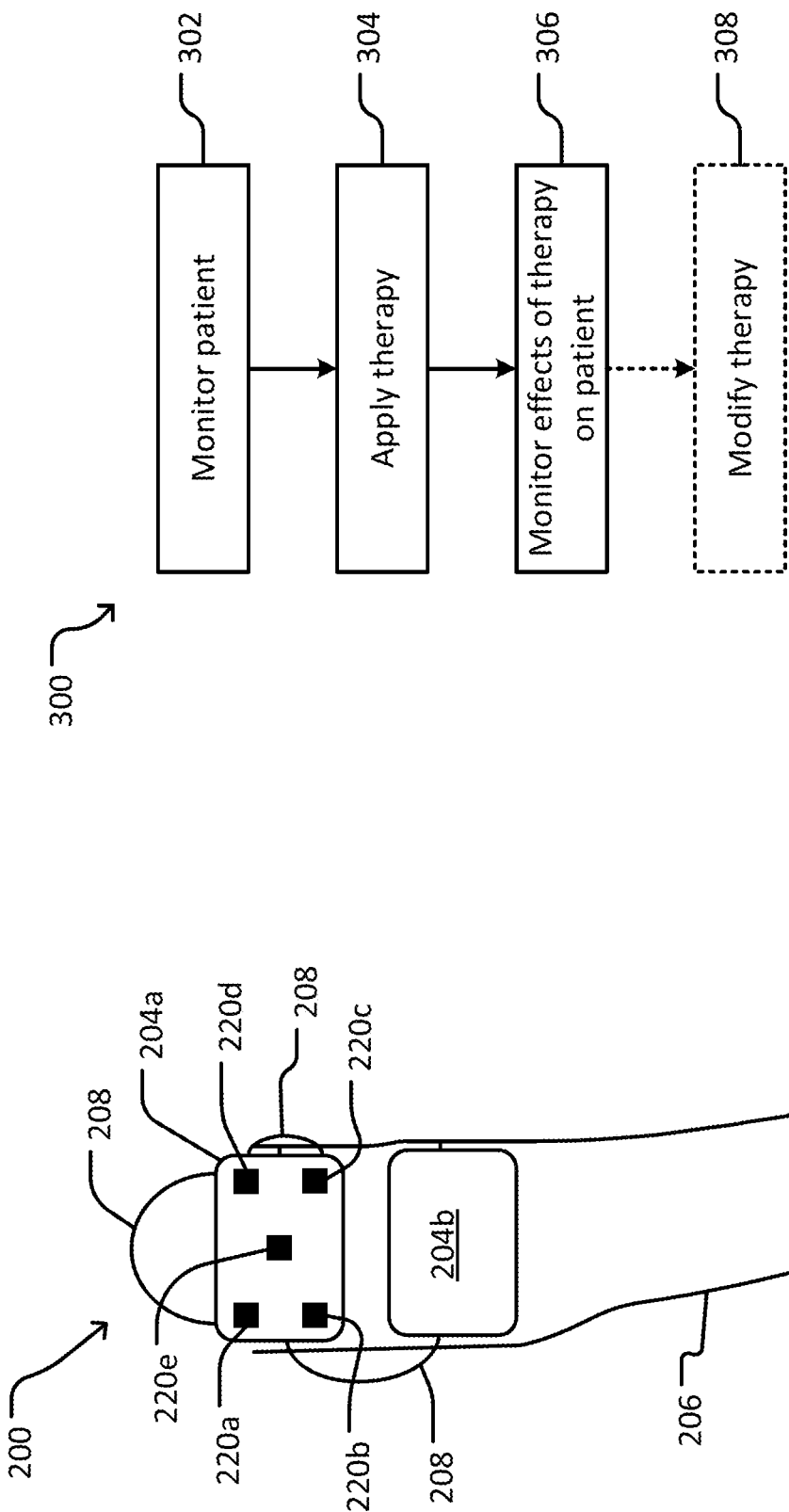

SYSTEMS AND METHODS FOR IMPLANTABLE DEVICES

CROSS-REFERENCE TO RELATED APPLICATIONS

This application claims the benefit of U.S. Provisional Application Ser. No. 62/618,432, filed Jan. 17, 2018. The disclosure of the prior application is considered part of (and is incorporated by reference in) the disclosure of this application.

BACKGROUND

1. Technical Field

This document relates to methods and materials for the treatment of pathological conditions, including arrhythmias and trauma, using temperature modulation via implantable devices. For example, this document relates to methods and devices for treating atrial and/or ventricular fibrillation by cooling the epicardium.

2. Background Information

Sudden cardiac arrest is the third leading cause of death of Americans. Resulting in more deaths each year than Alzheimer's disease, assault with firearms, breast cancer, colorectal cancer, diabetes, HIV, house fires, motor vehicle accidents, prostate cancer and suicides combined. More than 350,000 people die from sudden cardiac arrest each year in the United States.

Atrial fibrillation is the most common arrhythmia encountered in clinical practice, affecting over 2.5 million Americans. The risk of atrial fibrillation increases with advancing age, with a lifetime risk of developing the arrhythmia in 25% of all men and women 40 years of age or older. A Mayo Clinic study indicated that the burden of this disease will significantly grow with 16 million Americans expected to be afflicted by 2050.

Multiple prospective randomized trials have demonstrated the clinical benefit of implantable cardiac defibrillators (ICDs) in saving the lives of at-risk individuals, leading to their widespread adoption. A downside associated with ICD therapy, however, is the pain associated with defibrillation, whether shocks are delivered appropriately or inappropriately.

SUMMARY

This document describes methods and materials for the treatment of pathological conditions, including arrhythmias and trauma, using temperature modulation via implantable devices. For example, this document relates to methods and devices for treating atrial and/or ventricular fibrillation by cooling the epicardium.

In one aspect, this disclosure is directed to an implantable cooling device. The implantable cooling device can include a cooling element, two electrodes coupled to the cooling element, a memory that is capable of storing computer executable instructions, and a processor that can facilitate execution of the executable instructions stored in memory. The instructions can cause the processor to monitor, using the electrodes, a first parameter of a patient, apply, using the cooling element, a cooling therapy to the patient, and after applying therapy, monitor, using the electrodes, the first parameter of the patient as a feedback parameter.

In some cases, the instructions can also cause the processor to modify the cooling therapy based on the feedback parameter. In some cases, modifying the cooling therapy can include at least one of increasing an amplitude of the cooling therapy, decreasing an amplitude of the cooling therapy, increasing a duration of the cooling therapy, ceasing delivery of the cooling therapy, and continuing delivery of the cooling therapy. In some cases, the two electrodes can be at least one of a mechanical sensor, a piezoelectric crystal, a Doppler probe, and a blood pressure sensor. In some cases, the first parameter and the feedback parameter can be a conduction velocity and a feedback conduction velocity, respectively. In some cases, the conduction velocity and the feedback conduction velocity can be measured parallel to a Bachman's bundle of the patient.

In some cases, the instructions can cause the processor to detect when a patient is in flutter, conduct a nearest neighbor analysis, based on the nearest neighbor analysis, identify a primary vector of depolarization wavefront, and calculate the conduction velocity and the feedback conduction velocity using the two electrodes that align with the primary vector. In some cases, the first parameter and the feedback parameter can be a monophasic action potential and a feedback monophasic action potential, respectively. In some cases, the instructions can cause the processor to identify at least one of a linear increase or a non-linear increase using the feedback monophasic action potential, where the linear increase corresponds to direct cooling and non-linear increase corresponds to neural cooling.

In some cases, the first parameter and the feedback parameter can be an electrogram and a feedback electrogram, respectively. In some cases, the instructions can cause the processor to identify a baseline amplitude of the electrogram, identify an amplitude of the feedback electrogram, compare the amplitude to the baseline amplitude, and detect a decrease in the amplitude from the comparison of the amplitude to the baseline amplitude. In some cases, the decrease can be at least 25%. In some cases, the first parameter and the feedback parameter can be a Shannon entropy and a feedback Shannon entropy, respectively. In some cases, the instructions can cause the processor to generate a Shannon entropy map for the feedback parameter, and using the Shannon entropy map, calculate a degree of fibrillation versus organization to flutter. In some cases, the instructions can cause the processor to, when organization to flutter is present, continue applying the cooling therapy. In some cases, the instructions can cause the processor to generate electrical stimulation to be delivered using the two electrodes when a degree of disorder is determined to be detected. In some cases, the first parameter can be a ventricular rate, a blood pressure, or a neural recording. In some cases, the cooling element can include protrusions that can compress into myocardial tissue.

In another aspect, this disclosure is directed to a method of treating obesity. The method can include securing an implantable device in an omental of a patient, where the implantable element comprises a therapy element and an electrode, monitoring, using the electrode, a mobility of the omental, and when an increase in the mobility is detected, applying, using the therapy element, a heating therapy. In some cases, the method can include securing a second therapy element near a celiac ganglia of the patient. In some cases, the method can include applying a second therapy using the second therapy element.

Particular embodiments of the subject matter described in this document can be implemented to realize one or more of the following advantages. In some embodiments, heart conditions, such as arrhythmias and others, can be treated using the devices and methods provided herein. In some embodiments, arrhythmias can be treated by an implantable system for painlessly terminating arrhythmias. The devices and methods provided herein permit prompt termination of atrial fibrillation almost immediately after an episode begins (to prevent persistence) and is effective irrespective of patient age and comorbidities. In some cases, such conditions can be treated in a minimally invasive fashion using the devices and methods provide herein. Such minimally invasive techniques can reduce recovery times, patient discomfort, and treatment costs. Further, feedback can be used with cooling devices to provide detection of cooling and physiological effects of the cooling.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods and examples are illustrative only and not intended to be limiting.

The details of one or more embodiments of the invention are set forth in the accompanying drawings and the description below. Other features, objects, and advantages of the invention will be apparent from the description, drawings, and from the claims.

DESCRIPTION OF DRAWINGS

FIG. 3 is a diagram of the cooling device of FIG. 2, in accordance with some embodiments provided herein.

FIG. 4 is a method of providing therapy to a patient, in accordance with some embodiments provided herein.

Like reference numbers represent corresponding parts throughout.

DETAILED DESCRIPTION

This document describes methods and materials for the treatment of pathological conditions, including arrhythmias and trauma, using temperature modulation via implantable devices. For example, this document relates to methods and devices for treating atrial and/or ventricular fibrillation by cooling the epicardium.

Implantable cardiac defibrillators (ICDs) can aid saving the lives of at-risk individuals. A downside associated with ICD therapy, however, is the pain associated with defibrillation, whether shocks are delivered appropriately or inappropriately.

Some advantages of the methods and systems provided herein can include treating arrhythmias painlessly, or substantially painlessly, by an implantable system. Further, such conditions can be treated in a minimally invasive fashion using the devices and methods provide herein. Such minimally invasive techniques can reduce recovery times, patient discomfort, and treatment costs. Further, feedback can be used with cooling devices to provide detection of cooling and physiological effects of the cooling.

Figure 1:
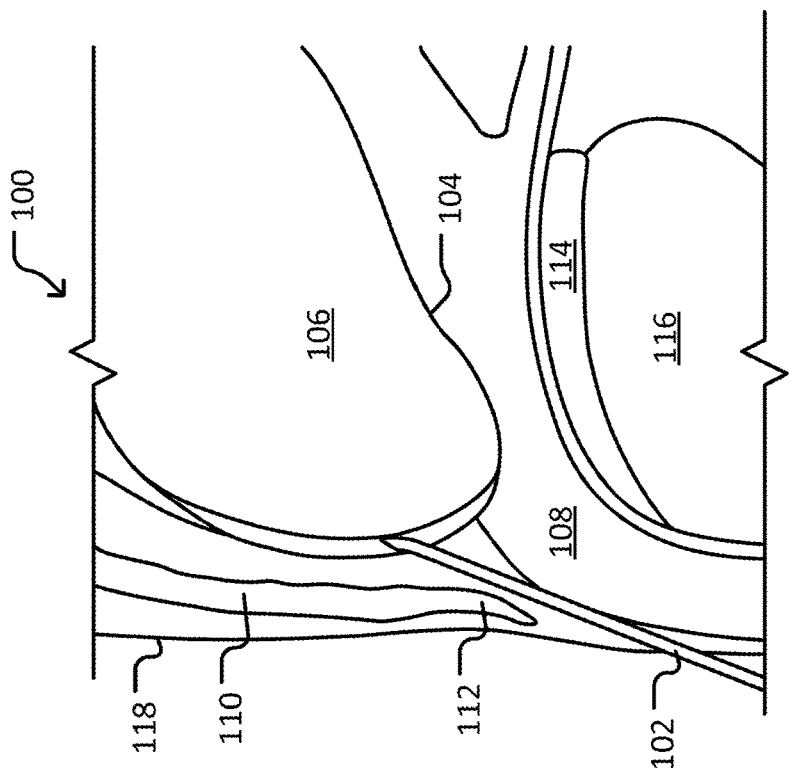
FIG. 1 is a lateral view of a device being inserted into a pericardium using a percutaneous epicardial access, in accordance with some embodiments provided herein.

Referring to FIG. 1, a device 102 being inserted into a pericardium 104 of a heart 106 of a patient 100 using percutaneous epicardial access is shown. When inserting device 102 in patient 100, device 102 punctures skin 118 at an upward angle. Device 102 should avoid the diaphragm 108, liver 114, and stomach 116. The upward angle allows these organs to be avoided and allows device 102 to maneuver under sternum 110, specifically the xiphoid process 112.

Figure 2:
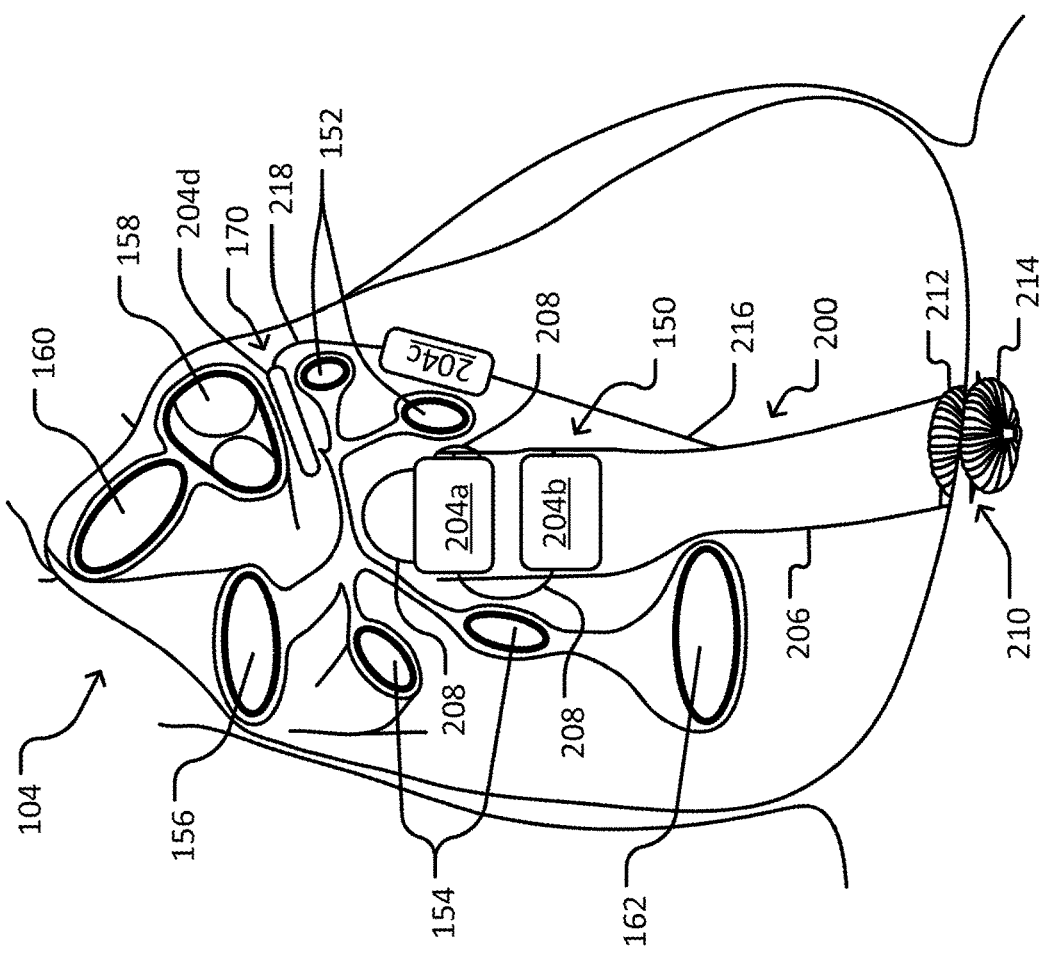
FIG. 2 is a diagram of a cooling device implanted in a pericardium, in accordance with some embodiments provided herein.

Referring to FIG. 2, a cooling device 200 implanted in a pericardium 104 of a heart is shown. As shown, the cooling device 200 can be located in the oblique pericardial sinus 150. In some cases, the cooling device 200 can include a plurality of cooling elements 204a, 204b, 204c, and/or 204d.

The cooling device 200 can be inserted into the pericardium 104 via aperture 210. Aperture 210 can be made using the techniques and devices described herein. In some cases, the cooling elements 204a, 204b, 204c, and/or 204d can be Peltier elements. Peltier elements can cause changes to the pericardium by fibrosis, cooling at the location of the cooling element 204a, 204b, 204c, and/or 204d.

Cooling device 200 (e.g., cooling elements 204a and 204b) can be implanted in the oblique pericardial sinus 150. Specifically, cooling device 200 can be located in the pericardium 104 between the left pulmonary veins 152 and the right pulmonary veins 154. Cooling device 200 can further be positioned below the superior vena cava 156, the left pulmonary artery 158, and the ascending aorta 160, and above the inferior vena cava 162.

In some cases, to achieve the desired placement, spacers can be delivered and positioned in the pericardium 104 (e.g., in the oblique pericardial sinus 150). In some cases, the spacer can be an expandable element. The spacer can be non-erosive. In some cases, the spacer is delivered with the cooling device 200. Alternatively, the spacer can be delivered separately from the cooling device 200.

In some cases, phalanges 208 can be used to secure the cooling device 200 in the desired location (e.g., the oblique pericardial sinus 150). In some cases, phalanges 208 are naturally recoiling phalanges that are attached to the device, but coil into spaces of the pericardium 104 (e.g., oblique pericardial sinus 150), providing fixation of the cooling device 200 in the pericardium 104.

In some cases, cooling device 200 can include an arm 216 that extends toward cooling elements 204c and/or 204d from wires 206. Arm 216 can naturally be drawn toward elements 204a and/or 204b (e.g., via shape memory techniques, a clip design, a spring, etc.). Arm 216 can aid in securing cooling element 204c on an opposite side of the left pulmonary veins 152 than the oblique pericardial sinus 150. In some cases, cooling element 204c can be fixed in place using cryo welding, as described above. In some cases, cooling element 204c can be inactive and function solely to provide mechanical stability to cooling device 200.

In some cases, the cooling device 200 can also include an arm 218 that extends from cooling element 204c towards cooling element 204d. Arm 218 can naturally be drawn toward elements 204a, 204b, and/or 204c (e.g., via shape memory techniques, a clip design, a spring, etc.). Arm 218 can aid in securing cooling element 204d in a transverse sinus 170 of the patient. In some cases, cooling element 204d can be fixed in place using cryo welding, as described above. In some cases, cooling element 204d can be inactive and function solely to provide mechanical stability to cooling device 200.

In some cases, the arrangement of cooling elements 204a, 204b, 204c, and/or 204d may be different based on the targeted areas of cooling. In some cases, cooling elements 204a, 204b, 204c, and/or 204d may provide cooling of the vein of Marshall, the oblique pericardial sinus 150, the transverse sinus 170, pulmonary veins 152/154, atrial appendages, other cardiac tissue, nerves, and/or central thoracic tissues.

In some cases, due to the variability of the oblique sinus 150, transverse sinus 170, and/or other locations (e.g., the left lateral sulcus) of the pericardium 104, the size and shape of the cooling device 200 and/or the cooling elements 204a, 204b, 204c, and/or 204d can be variable. In some cases, the cooling device 200 and/or the cooling elements 204a, 204b, 204c, and/or 204d can be expandable and the degree of expansion of the non-myocardial elements may be adjustable. In some cases, the expansion may be adjustable by an external modulatory element. For example, a screw or faucet-type turning element can be used as the external modulatory element. For example, the cooling device 200 and/or the cooling elements 204a, 204b, 204c, and/or 204d can be adjustable between 1.5 cm and 7 cm in width. For example, the cooling device 200 and/or the cooling elements 204a, 204b, 204c, and/or 204d can be adjustable between 1 cm and 5 cm in length. In some cases, computerized tomography (CT) and/or magnetic resonance imaging (MM) scans can be used to determine dimensions of the pericardium 104 such that the cooling device 200 can be 3D printed to fit the specific dimensions of the patient.

In some cases, size and shape variation of cooling device 200 can include a clip-like mechanism to a protruding finger element (e.g., cooling element 204c and/or 204d). In some cases, the protruding element can provide cooling to the vein of Marshal or across the fold of Marshall. In some cases, differential cooling can also be provided to the pulmonary vein, neural elements, and/or posterior left atrial tissue.

In some cases, cooling device 200 can include a sock or cover for the right and/or left atrial appendages. In some cases, such a sock or cover could provide myocardial cooling, neural, and/or venous cooling from the oblique and/or transverse sinus elements. In some cases, the sock or cover can be used for stabilizing the appendage. In some cases, the sock or cover can occlude one appendage (e.g., a left appendage), while cooling another appendage (e.g., a right appendage).

In some cases, cooling device 200 as described above can be used for prevention of stroke, fibrillation reduction, or a combination of both. In some cases, the cooling device 200 can be used for stability and cooling of the superior ganglia and appendage, which could be used as treatment for inappropriate sinus tachycardia or for stroke reduction.

Wires 206 can extend from the cooling elements 204a and 204b towards pericardium 104. In some cases, wires 206 can be antennas (e.g., an inductive antenna), such that cooling device 200 can communicate remotely. In some cases, remote communication can be with a device (e.g., a pulse generator) internal to the patient. In some cases, remove communication can be with a device (e.g., a power source, a controller, etc.) external to the patient. In some cases, wires 206 run through aperture 210 to other areas of the body (e.g., skin 118) or a generator (e.g., to power cooling device 200).

In some cases, wires 206 can be used to secure cooling device 200 to pericardium 104. In some cases, small clips can be placed on the edges of aperture 210. A ring shaped suture (e.g., securing elements 212 and/or 214) can be placed over a number of the clips, with overhanging wires to enclose the aperture 210. In some cases, a cryo element can be used to close aperture 210. In some cases, the cooling elements 204a, 204b, 204c, and/or 204d can be used to power the cryo element to gain fixity and closure of aperture 210. In some cases, the cooling elements 204a, 204b, 204c, and/or 204d can be used to gain fixity of the individual element to the overlying tissue (e.g., atrial myocardial fat) by cryo welding, preventing displacement. In some cases, to close aperture 210, opposing balloons or expandable elements may be used along wires 206.

Referring to FIG. 3, cooling device 200 is shown. In some cases, cooling device 200 can include electrodes 220a, 220b, 220c, 220d, and/or 220e.

In some cases, electrodes 220a, 220b, 220c, 220d, and/or 220e can be integrated into one or more of the cooling elements 204a, 204b, 204c, and/or 204d. In some cases, the cooling elements 204a, 204b, 204c, and/or 204d are Peltier elements and the electrodes 220a, 220b, 220c, 220d, and/or 220e are integrated with the Peltier elements. In some cases, electrodes 220a, 220b, 220c, 220d, and/or 220e can be located on non-cooling components of cooling device 200. In some cases, the electrodes 220a, 220b, 220c, 220d, and/or 220e can record unipolar, multipolar, bipolar, and/or omnipolar recordings.

In some cases, the cooling device 200 and/or the cooling elements 204a, 204b, 204c, and/or 204d can include a button and/or inverted V-shaped indentations. In some cases, the button and/or inverted V-shaped indentations can slightly and atraumatically compress into myocardial tissue. In some cases, the cooling device 200 and/or the cooling elements 204a, 204b, 204c, and/or 204d can include mechanical sensors, such as piezoelectric crystals and/or Doppler probes. In some cases, the cooling device 200 and/or the cooling elements 204a, 204b, 204c, and/or 204d can include impedance sensors. In some cases, the cooling device 200 and/or the cooling elements 204a, 204b, 204c, and/or 204d can include Peltier devices that have a gel backbone. In some cases, the gel backbone can be located posteriorly.

Still referring to FIGS. 3-4, in some cases, the cooling devices can include a sensor and/or electrode (not shown) to provide feedback. The sensors can provide information regarding cooling efficacy, unwanted heating, direct electrical and biological feedback, information regarding adjacent nervous tissue, etc. In some cases, the cooling elements 204a, 204b, 204c, and/or 204d can include thermal insulation elements to prevent injury to surrounding structures (e.g., esophagus, vagus nerve, phrenic nerve, etc.). In some cases, an impedance sensor, and/or an electrode, can be used in the pericardial space. The impedance sensor and/or electrode can be used to diagnose fibrillation, separately or in addition to another device (e.g., as a double-check). In some cases, the impedance sensor and/or electrode can detect atrial and/or ventricular fibrillation. In some cases, the impedance sensor and/or electrode can record neural signals (e.g., non-myocardial signals).

Referring to FIG. 4, a method 300 of providing therapy to a patient can include monitoring a patient at 302, applying a therapy to the patient at 304, monitoring the effects of the therapy on the patient at 306.

Monitoring a patient at 302 and monitoring the effects of the therapy on the patient at 306 can be substantially similar. Further, in some cases, the data collected at 302 and the data collected at 306 can be used in combination, such as with a comparison of the two. In some cases, monitoring a patient at 302 and/or 306 can include recording and/or calculating a conduction velocity, an action potential (e.g., a monophasic action potential), an electrogram, Shannon entropy, ventricular activity, blood pressure, and/or neural activity. In some cases, the recordation and/or calculations can be used for providing feedback regarding therapy.

In some cases, conduction velocity can be measured in sinus rhythm. In some cases, conduction velocity can be measured parallel to Bachman's bundle. Conduction velocity can be measured in a long axis of the transverse sinus 170 (e.g., cooling element 204*d*). In some cases, conduction velocity can be measured along a right to left, or left to right, axis of the oblique sinus 150 (e.g., cooling element 204*a* and/or 204*b*). In some cases, if the patient is in flutter, or flutter organizes during cooling, a nearest neighbor analysis can be done to identify a primary vector of a depolarization wavefront. Conduction velocity can be used to monitor the spreading of therapy over time. In some cases, the electrodes 220*a*, 220*b*, 220*c*, 220*d*, and/or 220*e* that line up best with the depolarization wavefront can be used to calculate the conduction velocity. In some cases, the tissue local to the site of therapy can show different effects than the tissues more distal to the site of therapy. In some cases, multiple conduction velocities can be measured and compared to determine how therapy is progressing. In some cases, conduction velocity can be determined by pacing from a first electrode and monitoring the amount of time it takes for pacing to reach other electrodes.

In some cases, monophasic action potential can be used for feedback. In some cases, the action potential duration and/or refractory period can show a linear increase with direct cooling. In some cases, the action potential duration and/or refractory period can show a nonlinear effect. In some cases, the nonlinear effect can suggest additional autonomic neural cooling. In some cases, the nonlinear effects can enhance or decrease a natural slope relating to cooling with repolarization. In some cases, electrodes being indented into tissue can create a signal corresponding to the plunge of the electrode into the tissue. In some cases, the time that it takes for the signal to return to a baseline (e.g., repolarization time) can be monitored.

In some cases, an electrogram can be collected at 302 and at 306. In some cases, a bipolar electrogram amplitude showing a decrease (e.g., up to about 25%) can suggest cooling effects. In some cases, the amplitude decrease can indicate the cooling effects are occurring without permanent loss of myocardial function. In some cases, the electrogram can be used to identify regularization of electrogram amplitude refractoriness or timing as a surrogate for organization of the arrhythmia. In some cases, the electrogram can vary in shape depending on a depth of cooling. If an electrogram shows wider cooling, a greater depth of cooling can be determined. In some cases, if an electrogram shows narrower cooling, it can be determined that superficial cooling is occurring.

In some cases, the mechanical sensors integrated into the elements can be used to monitor atrial myocardial function. The mechanical sensors can monitor atrial myocardial function to determine if myocardial function is normal and/or becoming regular. In some cases, the mechanical sensors can be used as a cross-check for whether the signals being recorded by the device are neural or myocardial in origin. In some cases, a particular high-frequency signal could be ganglia/neural or myocardial. In some cases, mechanical movement of the atrium can mirror a myocardial origin electrogram, however, the electrogram would have no relationship with ganglia or neural firing.

In some cases, Shannon entropy maps generating software can be integrated into omnipolar recording from the electrodes 220*a*, 220*b*, 220*c*, 220*d*, and/or 220*e*. In some cases, the Shannon entropy map can be used to calculate a degree of fibrillation versus organization to flutter. In some cases, if significant organization is present, cooling can continue and/or reinitiate when initial cooling is ineffective (e.g., during modifying therapy at 308). In some cases, if the degree of disorder decreases significantly to preset detection values. In some cases, when the degree of disorder reaches the preset detection values, the electrodes 220*a*, 220*b*, 220*c*, 220*d*, and/or 220*e* can provide rapid stimulation.

In some cases, rapid stimulation can terminate the flutter. In some cases, after stimulation, Shannon entropy maps can be monitored in case pacing is proarrhythmic, more disorganization results, and/or sinus rhythm results. In some cases, stimulation can be delivered until sinus rhythm occurs.

In some cases, ventricular activity can be recorded. In some cases, the effects of ventricular rate can be detected as a surrogate for autonomic modulation and restoration of rhythm. In some cases, when a change in ventricular activity occurs, therapy can be paused.

In some cases, blood pressure can be measured using blood pressure sensors or impedance sensors. In some cases, blood pressure can be measured using a posteriorly located ascending aorta compression of the gel backbone of the device (e.g., cooling device 200 and/or elements 204*a*, 204*b*, 204*c*, and/or 204*d*).

In some cases, neural activity can originate from either the vagus nerve posteriorly or the retroatrial cardiac ganglia anteriorly. In some cases, the neural activity can be measured from the posterior backbone of the device (e.g., cooling device 200 and/or elements 204*a*, 204*b*, 204*c*, and/or 204*d*). In some cases, the ganglia activity can be measured from electrodes (e.g., electrodes 220*a*, 220*b*, 220*c*, 220*d*, and/or 220*e*) on the device (e.g., cooling device 200 and/or elements 204*a*, 204*b*, 204*c*, and/or 204*d*). In some cases, neural activity can be used to provide feedback regarding modulation of the energy for titration. In some cases, the neural activity can be used to provide feedback to aid in cooling of nerves. In some cases, cooling of nerves can be used to treat arrhythmia, gastric hypermotility, and/or appetite regulation. In some cases, these treatments can occur simultaneously. In some cases, the phrenic nerve should be avoided when providing therapy.

Applying a therapy to the patient at 304 can include applying a therapy via a device (e.g., cooling device 200, elements 204*a*, 204*b*, 204*c*, and/or 204*d*, and/or electrodes 220*a*, 220*b*, 220*c*, 220*d*, and/or 220*e*). In some cases, therapy can be a thermal therapy, such as cooling or heating. In some cases, therapy can be an electrical therapy (e.g., stimulation, electroporation, titration, etc.).

In some cases, therapy can be provided to aid in treating obesity. For example, a device can be located in an omental and when an increase in mobility is detected (e.g., when eating, or just prior to eating), the stomach cools. The device can dissipate heat in the proximal jejunum and duodenum, forcing energy losses from the body as the body attempt to cool the area (e.g., by increasing blood flow). In some cases, a device, or a portion of the device, can be placed near the celiac ganglia. This device could additionally, or independently, modify motility and appetite. In some cases, applying a therapy can include applying a therapy for hypertension. In some cases, treatment of hypertension can be delivered via devices that are located in or near vascular locations, extravascular locations, renal nerves, and/or aortic nerves. In some cases, hypertension therapy can use pressure feedback to monitor therapy. In some cases, therapy can include providing intermittently cooling of the myocardium to improve myocardial relaxation. In some cases, the therapy can be provided to cool a muscle (e.g., via a sock type device). In some cases, the sock type device can be a fabric or chain-mail type device. In some cases, the therapy can aid in occluding an appendage. In some cases, the therapy can aid in maintaining sinus rhythm. In some cases, the therapy can aid in preventing stroke. In some cases, the therapy can aid in rhythm management. In some cases, one atrial appendage can be closed (e.g., by a sock) and another appendage can receive cooling therapy.

Monitoring the effects of the therapy on the patient at 306 can include monitoring the same parameters as were monitored at 302. These parameters can be compared and/or analyzed to determine results of the cooling and/or therapy that was applied at 304. Monitoring the effects of the therapy on the patient at 306 can provide feedback relating to the effects of therapy. In some cases, a combination of the parameters recorded can be used to optimize therapy. In some cases, sensors that record electrical and/or mechanical parameters can be given a greater weight than other parameters. In some cases, different weights can be given to parameters recorded from different locations (e.g., via different electrodes). For example, in some cases, electrodes facing the heart can have a different weight than electrodes on the pericardial surface of the device.

In some cases, method 300 can also include modifying therapy at 308. Modifying therapy at 308 can include adjusting, reapplying, stopping, and/or continuing therapy. In some cases, therapy can be increased or decreased. In some cases, a location of therapy can be modified. In some cases, a therapy can be changed from one type of therapy to a second type of therapy.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. An implantable cooling device, the device comprising:
    a cooling element configured to contact and cool an oblique pericardial sinus of a patient;
    two or more electrodes coupled to the cooling element, the two or more electrodes configured to detect an atrial fibrillation of the patient;
    a memory that is capable of storing computer executable instructions; and
    a processor that is configured to facilitate execution of the computer executable instructions stored in the memory, wherein the computer executable instructions cause the processor to:
        monitor, using the two or more electrodes, a first electrogram of the patient;
        after monitoring the first electrogram, apply, using the cooling element, a cooling therapy to the oblique pericardial sinus of the patient;
        after or while applying the cooling therapy, monitor, using the two or more electrodes, one or more feedback electrograms;
        compare the first electrogram and the one or more feedback electrograms on an amplitude basis;
        determine, based on the comparison of the first electrogram and the one or more feedback electrograms, whether to adjust one or more parameters of the cooling therapy and/or to deliver additional cooling therapy from the cooling element;
        after or while applying the cooling therapy, monitor a conduction velocity of the patient over time; and
        determine, based on the monitoring of the conduction velocity, whether to adjust one or more parameters of the cooling therapy and/or to deliver additional cooling therapy from the cooling element.

2. The device of claim 1, wherein the computer executable instructions further cause the processor to modify the cooling therapy based on the one or more feedback electrograms.

3. The device of claim 2, wherein modifying the cooling therapy based on the one or more feedback electrograms comprises at least one of increasing an amplitude of the cooling therapy, decreasing an amplitude of the cooling therapy, increasing a duration of the cooling therapy, ceasing delivery of the cooling therapy, and continuing delivery of the cooling therapy.

4. The device of claim 1, further comprising at least one of a mechanical sensor and a blood pressure sensor, wherein the mechanical sensor comprises at least one of a piezoelectric crystal and a Doppler probe.

5. The device of claim 1, wherein the conduction velocity and the feedback conduction velocity are measured parallel to a Bachman's bundle of the patient.

6. The device of claim 1, wherein the computer executable instructions further cause the processor to:
    detect when the patient is in flutter;
    conduct a nearest neighbor analysis;
    based on the nearest neighbor analysis, identify a primary vector of depolarization wavefront; and
    calculate the conduction velocity and the feedback conduction velocity using the two or more electrodes that align with the primary vector of depolarization wavefront.

7. The device of claim 1, wherein the computer executable instructions cause the processor to monitor a first monophasic action potential and a feedback monophasic action potential.

8. The device of claim 7, wherein the computer executable instructions further cause the processor to:
using the feedback monophasic action potential, identify at least one of a linear increase or a non-linear increase between the first monophasic action potential and the feedback monophasic action potential, wherein the linear increase between the first monophasic action potential and the feedback monophasic action potential corresponds to direct cooling and the non-linear increase between the first monophasic action potential and the feedback monophasic action potential corresponds to neural cooling.

9. The device of claim 1, wherein the computer executable instructions cause the processor to monitor a first Shannon entropy and a feedback Shannon entropy.

10. The device of claim 9, wherein the computer executable instructions further cause the processor to:
generate a Shannon entropy map; and
using the Shannon entropy map, calculate a degree of fibrillation versus organization to flutter.

11. The device of claim 10, wherein the computer executable instructions further cause the processor to, when organization to flutter is present, continue applying the cooling therapy.

12. The device of claim 10, wherein the computer executable instructions further cause the processor to:
when a degree of disorder is determined to be detected, generate electrical stimulation to be delivered using the two or more electrodes.

13. The device of claim 1, wherein the computer executable instructions cause the processor to monitor at least one of a ventricular rate, a blood pressure, and a neural recording.

14. The device of claim 1, wherein the cooling element comprises protrusions configured to compress into myocardial tissue.

15. The device of claim 1, further comprising a phalange attached to the implantable cooling device, the phalange configured to coil into a space of a pericardium, thereby providing fixation of the implantable cooling device in the pericardium.

16. An implantable cooling device, the device comprising:
a cooling element configured to contact and cool an oblique pericardial sinus of a patient;
two or more electrodes coupled to the cooling element, the two or more electrodes configured to detect an atrial fibrillation of the patient;
a memory that is capable of storing computer executable instructions; and
a processor that is configured to facilitate execution of the computer executable instructions stored in the memory, wherein the computer executable instructions cause the processor to:
monitor, using the two or more electrodes, a first electrogram of the patient;
after monitoring the first electrogram, apply, using the cooling element, a cooling therapy to the oblique pericardial sinus of the patient;
after or while applying the cooling therapy, monitor, using the two or more electrodes, one or more feedback electrograms;
identify a baseline amplitude of the first electrogram;
identify an amplitude of the one or more feedback electrograms;
compare the amplitude of the feedback electrogram to the baseline amplitude of the electrogram;
determine, based on the comparison of the amplitude of the one or more feedback electrograms to the baseline amplitude of the first electrogram, whether to adjust one or more parameters of the cooling therapy and/or to deliver additional cooling therapy from the cooling element;
detect a decrease in the amplitude of the one or more feedback electrograms based on the comparison of the amplitude of the one or more feedback electrograms to the baseline amplitude of the electrogram; and
detect, based on the decrease in the amplitude of the one or more feedback electrograms, a cooling effect of the cooling therapy.

17. The device of claim 16, wherein the decrease in the amplitude of the one or more feedback electrograms is at least 25%.

18. The device of claim 16, wherein a shape of the one or more feedback electrograms varies depending on a depth of cooling.

19. A method of treating obesity, the method comprising:
implanting an implantable device in contact with an omentum of a patient, wherein the implantable device comprises:
a temperature modulation element;
an electrode;
a memory that is capable of storing computer executable instructions; and
a processor that is configured to facilitate execution of the computer executable instructions stored in the memory;
monitoring, using the implantable device in contact with the omentum, a movement of the omentum caused by or resulting from digestion; and
when an increase in the movement of the omentum is detected, transferring heat energy, using the implantable device in contact with the omentum, between: i) the omentum, and ii) a proximal jejunum and/or a duodenum.

20. The method of claim 19, further comprising securing a second temperature modulation element near a celiac ganglia of the patient.

* * * * *